United States Patent [19]

Juvinall

[11] Patent Number: 5,214,713
[45] Date of Patent: May 25, 1993

[54] CONTAINER INSPECTION SYSTEM WITH SYSTOLIC ARRAY PROCESSING

[75] Inventor: John W. Juvinall, Ottawa Lake, Mich.

[73] Assignee: Owens-Brockway Glass Container Inc., Toledo, Ohio

[21] Appl. No.: 684,646

[22] Filed: Apr. 12, 1991

[51] Int. Cl.⁵ .............................................. G06K 9/00
[52] U.S. Cl. ................... 382/8; 250/223 B; 358/106; 382/27; 382/49
[58] Field of Search ................ 382/27, 41, 49, 8; 358/106, 101; 250/223 B

[56] References Cited

U.S. PATENT DOCUMENTS

| | | | |
|---|---|---|---|
| 4,230,219 | 10/1980 | Pezzin et al. | 198/481 |
| 4,363,104 | 12/1982 | Nussmeier | 382/41 |
| 4,378,493 | 3/1983 | Dorf et al. | 250/223 B |
| 4,378,494 | 3/1983 | Miller | 250/223 B |
| 4,378,495 | 3/1983 | Miller | 250/223 B |
| 4,550,437 | 10/1985 | Kobayashi et al. | 382/27 |
| 4,701,612 | 10/1987 | Sturgill | 250/223 B |
| 4,817,175 | 3/1989 | Tenenbaum et al. | 382/49 |
| 4,901,360 | 2/1990 | Shu et al. | 382/27 |
| 4,958,223 | 9/1990 | Juvinall | 358/106 |

OTHER PUBLICATIONS

Manufacturer Data Sheets (NCR-Geometric Arithmetic Parallel Processor (NCR45CG72) (1984).

Primary Examiner—Leo H. Boudreau

[57] ABSTRACT

A system for inspecting containers that includes a camera for obtaining an image of the container that comprises a plurality of pixels each forming a portion of the image, and a memory for receiving and storing image pixel data from the camera. A systolic array processor includes a plurality of one-bit data processors configured in a rectangular array, and a microcoded controller for controlling operation of the plurality of one-bit data processors to process data simultaneously and in parallel. A data-dependent processor separate from the systolic array processor is adapted to perform non-sequential and/or data-dependent processing of image data. A master computer is connected to the camera control electronics, memory, systolic array processor and data-dependent processor. By controlling operation of these electronics, the master computer obtains pixel data from the camera and stores such data by pixel in memory, retrieves pixel data from memory and loads such data by pixel into the systolic array processor such that each of the plurality of one-bit processors receives and operates on one byte of pixel data, returns data from the systolic array processor to the memory, and retrieves pixel data from memory and loading such data into the data-dependent processor for non-sequential and/or data-dependent image processing.

14 Claims, 5 Drawing Sheets

CONTAINER INSPECTION SYSTEM WITH SYSTOLIC ARRAY PROCESSING

The present invention is directed to machine vision systems having particular utility for inspection of transparent containers, and more particularly to a system for inspecting containers for commercial variations and geometric characteristics.

BACKGROUND AND OBJECTS OF THE INVENTION

Conventional technology for mass production of glass or plastic containers involves forming the containers in a multiplicity of blow-molds. Various types of faults or checks, termed "commercial variations" in the art, may occur. It has heretofore been proposed to employ optical scanning techniques for inspecting such containers for variations that affect optical transmission characteristics of the container sidewall. In U.S. Pat. Nos. 4,378,493, 4,378,494 and 4,378,495, all of which are assigned to the assignee of the present application, there are disclosed methods and apparatus in which glass containers are conveyed through a plurality of stations where they are physically and optically inspected. At one inspection station, a glass container is held in vertical orientation and rotated about its vertical axis. An illumination source directs diffused light energy through the container sidewall. A camera, which includes a plurality of light sensitive elements or pixels oriented in a linear array parallel to the vertical axis of container rotation, is positioned to view light transmitted through a vertical strip of the container sidewall. The output of each pixel is sampled at increments of container rotation, and event signals are generated when adjacent pixel signals differ by more than a preselected threshold level. An appropriate reject signal is produced and the rejected container is sorted from the conveyor line.

U.S. Pat. No. 4,701,612, assigned to the assignee hereof, discloses a method and apparatus for inspecting the finish of transparent containers, particularly glass containers, that include facility for directing diffused light energy laterally through the container finish as the container is rotated about its central axis. A camera includes a plurality of light sensitive elements or pixels disposed in a linear array angulated with respect to the container axis and coplanar therewith to view the external and internal finish wall surfaces, the latter through the open container mouth. Individual elements of the camera linear array are sampled by an information processor at increments of container rotation, and corresponding data indicative of light intensity at each element is stored in an array memory as a combined function of element number and scan increment. Such data is compared following completion of container rotation to standard data indicative of an acceptable container finish, and a reject signal is generated if such comparison exceeds an operator-adjustable threshold.

U.S. Pat. No. 4,958,223, also assigned to the assignee hereof, discloses apparatus for inspecting the finish of a container as the container is rotated about its central axis. A light source is positioned to direct diffused light energy onto the container finish, and a camera is positioned across the axis of the container from the light source. The camera comprises a CCD image array sensor having a matrix of image sensing elements arranged in a row-and-column array with transport registers and gating electronics on the sensor for selectively reading image data at the sensing elements sequentially by row and column. Image processing electronics is coupled to the array and generates camera control signals for selectively integrating data from adjacent columns and/or rows on the image array sensor, and for downloading data from the sensor to the image processing electronics only from image data areas of interest. In this way, not only is signal-to-noise ratio enhanced by performing data processing on the sensor itself, but also image processor memory is saved by downloading data only from image areas of interest.

Although the systems and techniques disclosed in the abovenoted patents represent a significant advance in previous inspection technology, improvements remain desirable. For example, image processing computers disclosed in the noted patents comprise conventional VonNeuman processors. These processors are extremely efficient in performing data-dependent processing in which the processor performs some function on a particular pixel, and then branches in the program dependent upon the result of that operation and therefore the value of the pixel. These processors are also efficient in handling non-sequential processing instructions, and many types of non-standard image algorithms. However, many image processing techniques require identical processing of large amounts of image data, such as for signal filtering or comparison to a signal threshold, which are inefficient and time-consuming in VonNeuman-type processors. This problem becomes particularly acute in machine vision system applications, such as applications involving inspection of transparent containers, where rapid processing is required to support high-volume mass production. It is therefore a general object of the present invention to provide a machine vision system that finds particular utility in inspection of transparent containers for variations that affect commercial quality thereof, and in which the architecture of the image processing electronics is constructed for enhanced efficiency of both sequential and non-sequential processing of image data.

SUMMARY OF THE INVENTION

A machine vision system in accordance with one aspect of the present invention includes a camera for obtaining an image that comprises a plurality of pixels each forming a portion of the image, and a memory for receiving and storing image pixel data from the camera. A systolic array processor includes a plurality of one-bit data processors configured in a rectangular array, and a microcoded controller for controlling operation of the plurality of one-bit data processors to process data simultaneously and in parallel. A data-dependent processor separate from the systolic array processor is adapted to perform non-sequential and/or data-dependent processing of image data. A master computer is connected by data and control buses to the camera control electronics, memory, systolic array processor and data-dependent processor. By controlling operation of these electronics, the master computer obtains pixel data from the camera and stores such data by pixel in memory, retrieves pixel data from memory and loads such data by pixel into the systolic array processor such that each of the plurality of one-bit processors receives and operates on one byte of pixel data, returns data from the systolic array processor to the memory, and retrieves pixel data from memory and loads such data into the data-dependent processor for non-sequential and/or data-dependent image processing.

Provision of separate systolic array and data-dependent processors, with operation thereof controlled by a separate master computer, permits each type of processor to perform functions for which it is best suited, thereby enhancing overall efficiency of the system. The data-dependent processor can efficiently process algorithms with a high degree of data dependency, or which operate on only a small portion of the overall image. Typical image processing applications for what the data-dependent processor would be suitable include container edge detection algorithms where an edge pixel must be located and adjacent pixels scanned dependent on the location of the edge pixel, and measuring container diameter or wobble requiring mathematical calculations. The systolic array processor can perform parallel sequential processing on large amounts of image data. Typical image-processing applications for which the systolic array processor would be suitable include filtering of image pixel data, comparison of image pixel data bytes to a threshold or to each other for fault detection or other purposes, and highlighting of the finish edge for measuring diameter or detecting wobble in algorithms that allow all of the edge pixels to be found independently and simultaneously—i.e., in parallel. Furthermore, the master computer may select between the data-dependent processor and the systolic array processor for performing non-standard image processing algorithms.

It should be noted at this point that the terms "systolic array processor" and "data-dependent processor" are intended to describe the structures of the respective processors rather than the character of the processing performed therein. A systolic array processor can perform some types of highly parallel data-dependent processing. For example, the systolic array processor can execute an algorithm on a complete block of data (as will be described) and set a plane of flags dependent on the data. Processing can then be performed in parallel for every pixel where a flag is set. Systolic array processors are uniquely adapted to execute processing that is highly parallel in nature, and on the other hand are not well suited to execute processing that is not highly parallel in nature, such as mathematical calculations. The data-dependent processor is provided to execute such non-parallel processing.

Thus, the data-dependent processor of the present invention can be envisioned as a multiple-instruction-multiple-data (MIMD) processor that complements the capabilities of the single-instruction-multiple-data (SIMD) systolic array processor. In the SIMD array, a single processing instruction stream operates on a large parallel data array. On the other hand, the MIMD processor is highly efficient at processing data-dependent algorithms that are dependent on single or small amounts of data. An array architecture of MIMD processors also allows simultaneous processing of different tasks where each task involves a different algorithm operating on different data. Each MIMD processor should be of VonNeuman, Harvard or similar CISC or RISC architecture.

In accordance with another feature of the invention, electronics are provided for controlling access to the common memory by the separate data processors. The memory access electronics includes separate interfaces coupled to the systolic array processor for loading data into and retrieving data from the systolic array processor, and a third interface coupled to the camera for obtaining pixel data from the camera. Each interface is connected to the common memory and includes separate memory for permitting the memory access interfaces to function simultaneously, thereby further enhancing efficiency of operation of the overall system.

The data-dependent processor comprises at least one processor, and preferably a plurality of closely coupled VonNeuman processors. Each VonNeuman processor has an associated multi-byte register interconnecting the processor to the data bus. The common memory is responsive to a data request from a VonNeuman processor to load multiple sequential data bytes from memory into the multi-byte register associated with that processor. Each VonNeuman processor searches for desired data in its associated register before requesting data from the master controller. Since most image processing algorithms involve a substantial degree of sequential data processing, this technique saves substantial time by reducing the number of occasions on which the processor requires access to the data bus and common memory, which must also be accessed by the other elements of the image processing electronics.

Image data is transferred between the memory and the systolic array processor in a bit-parallel configuration serially by byte, at least one byte at a time. The systolic array processor includes a rectangular array of $N \times M$ processors, and each pixel data byte comprises n bits, $0, 1, \ldots n-1$. The systolic array processor includes a first systolic array of $N \times n$ processors that receive $N \times M$ bytes of bit-parallel pixel data in sequence by byte. A second systolic array of $N \times M$ processors receive pixel data byte-parallel by bit from the first array under control of microcoded control electronics. Following byte-parallel processing in the second processor array, the processed pixel data is transferred byte-parallel by bit from the second array to the first array, and then bit parallel by byte from the first array back to the memory. Thus, in accordance with this feature of the invention, bit-parallel image pixel data in memory is efficiently prepared for bit-serially loading into and processing in the one-bit processors of the second systolic array, and efficiently reconverted to bit-parallel data format for restorage in the memory.

In accordance with a further feature of the invention, the image is effectively divided at the camera into a plurality of data areas of interest as disclosed at above-noted U.S. Pat. No. 4,958,223, and image data is grouped by data area as stored in memory during sequential scans of the camera. That is, image pixel data from a first of the camera data areas is stored in first sequential locations of memory as a function of image scan, and image pixel data from the second and any subsequent data areas of interest are correspondingly loaded in second and subsequent locations in memory, separate from the first location, as a function of container scan. Since image processing algorithms, particularly for inspection of transparent containers, typically involve comparison of image pixel data from specific image data areas obtained on sequential image scans, this feature of the invention enhances efficiency of such subsequent processing by grouping pixel data in memory by data area. This allows rapid and efficient storage and retrieval of data to and from memory.

A further feature of the invention contemplates retrieval of pixel data from memory for processing in the systolic array in sequential overlapping blocks of memory data. Since many image processing algorithms involve comparison of adjacent image pixel data, this feature eliminates errors and obscurities that would otherwise result from inability to compare adjacent pixels in adjacent data blocks if the data blocks were not overlapping as retrieved for processing. Such data block retrieval is controlled in the first instance by the master computer, which commands the memory access electronics to retrieve blocks of data from memory and transfer the data to the systolic array processor. The command states the location of the data block, the size of the systolic array, the amount of overlap with adjacent data blocks, etc. The memory access electronics then retrieves the data from memory, byte by byte. The master computer may also command the data-dependent processor to perform a particular vision task. The data-dependent processor then determines what data is needed from memory, and retrieves the data as required. The master computer thus cooperates with microcoded controllers associated with the other individual system elements for controlling data movement.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
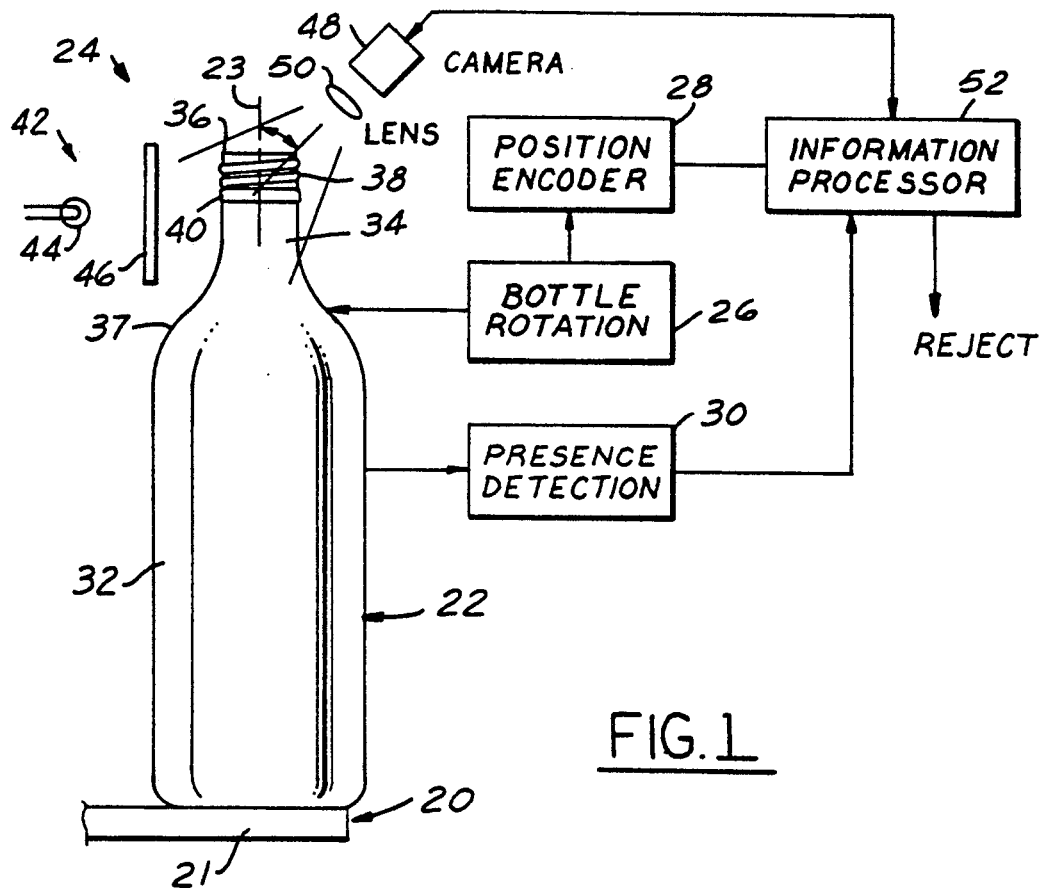
FIG. 1 is a functional block diagram of a system for inspecting the finish of transparent containers in accordance with one presently preferred implementation of the invention.

Referring to FIG. 1, a conveyor 20, typically including a starwheel (not shown) and a slide plate 32, is so disposed and connected to a source of molded containers as to bring successive containers 22 into position at a finish inspection station 24. Conveyor 20 may be of any suitable type, such as those shown in U.S. Pat. Nos. 4,230,219 and 4,378,493, the disclosures of which are incorporated herein by reference for background, and would typically include a rotatable starwheel for bringing successive containers into position and holding the containers in fixed position during the scanning operation. A bottle rotating device 26, such as a drive roller, is positioned to engage container 22 at station 24 and to rotate the container about its central axis 23. An encoder 28 is coupled to the container rotation mechanism to provide signals indicative of increments of container rotation. A detector 30, such as a limit switch, is positioned to provide a signal indicative of presence of container 22 at station 24.

In the preferred implementation of the invention herein discussed, container 22 is illustrated as a molded glass bottle having a container body 32 and a generally cylindrical neck 34 that projects upwardly from the body shoulder 37. The finish portion of the container inspected in accordance with the present invention includes the upper portion of neck 34 that terminates in a cap sealing surface 36. A helical thread 38 is integrally molded onto the outer surface of the finish wall that surrounds the container mouth, and a lip or shoulder 40 is likewise formed on the finish wall outer surface over which a cap skirt may be crimped in the usual manner for affixing the cap to the container. In general, the present invention is disclosed in conjunction with apparatus adapted to inspect that portion of the container finish to which the cap is to be affixed. It will be appreciated as the description unfolds, however, that the system of the present invention is equally well adapted for inspection of the container-sidewall, for example, and indeed for many other types of machine visions applications.

A light source 42 is positioned to direct diffused light energy onto the container finish from a direction generally lateral to container axis 23. Light source 42 includes one or more lamps 44 and a diffuser plate 46. A camera 48 is positioned on the side of axis 23 opposite to light source 42 to receive an image (FIG. 2) of the container finish through a camera lens 50. An information processor 52 receives a signal from detector 30 indicative of presence of a container 22 at inspection station 24, and signals from encoder 28 indicative of increments of container rotation. Camera 48 is likewise coupled to information processor 52 for receiving scan control signals and providing signals indicative of the intensity of light incident on each camera element. Information processor 52 has an output for providing a reject signal to container sorting apparatus (not shown).

Figure 2:
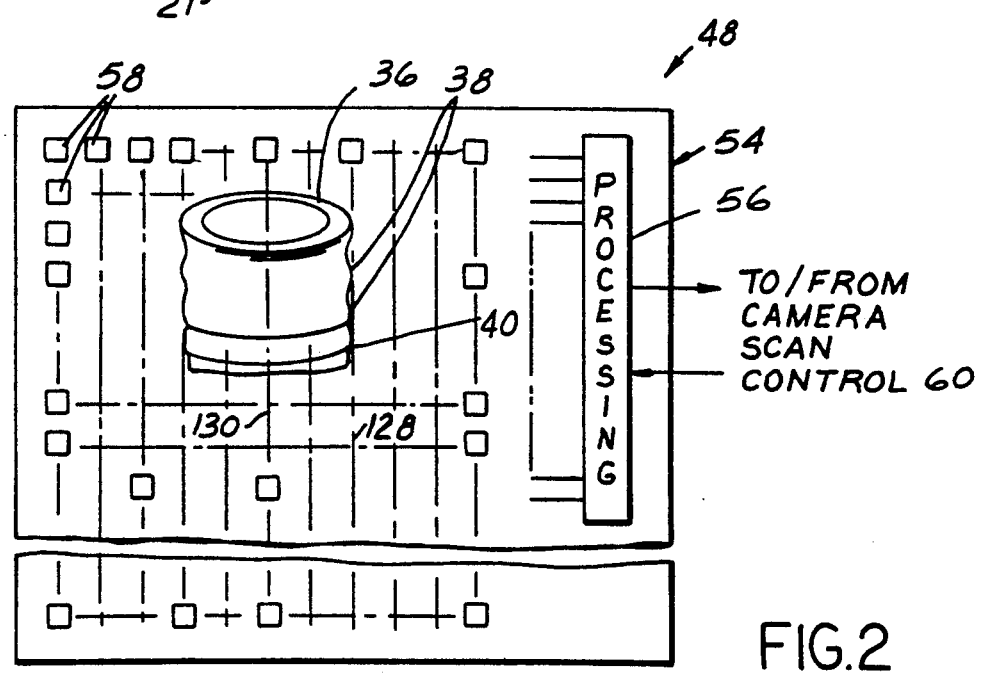
FIG. 2 is a schematic illustration of the container finish as viewed by the camera of FIG. 1 with camera field of view superimposed thereon.
Figure 3:
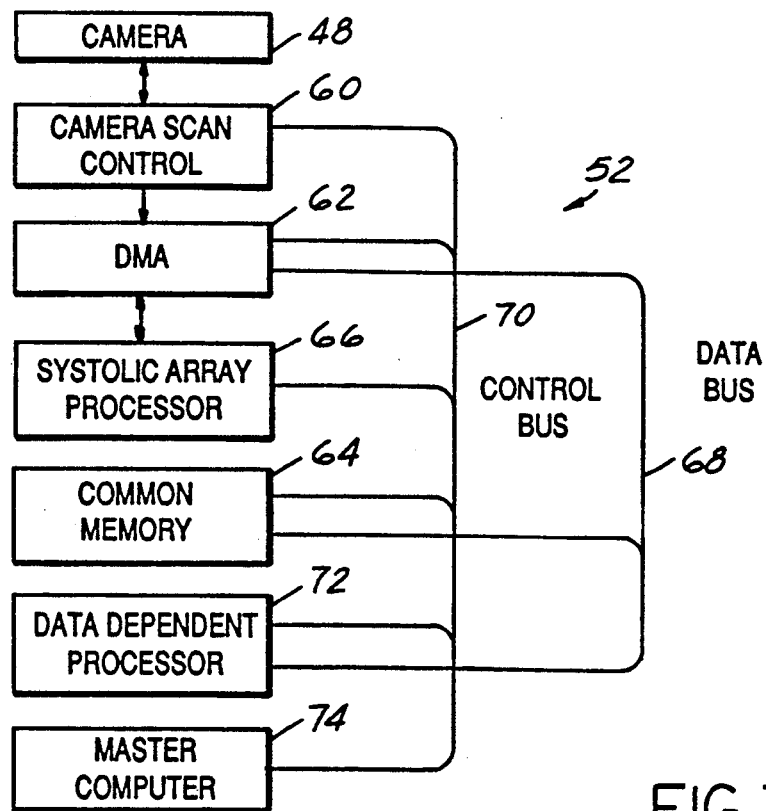
FIG. 3 is a functional block diagram of the information processor illustrated in FIG. 1.

As shown in FIG. 2, camera 48 preferably comprises a monolithic matrix array sensor in the form of a solid-state charge coupled device (CCD) having on-board processing electronics 56. A plurality of CCD sensing elements 58 are disposed in a row-and-column array on sensor 54, and are connected by suitable shift registers (not shown) to processing electronics 56. The image of the finish of container 22 is directed onto array sensor 54 by lens 50, as schematically illustrated in FIG. 2. Processing electronics 56 provides image pixel data signals to, and receives control signals from, the camera scan control electronics 60 (FIG. 3). To the extent thus far described, the system of FIGS. 1 and 2 is substantially identical to that disclosed in conjunction with FIGS. 1, 6 and 7 of above-noted U.S. Pat. No. 4,958,223, which also discloses a presently preferred embodiment of camera scan control electronics 60 (FIG. 3). The disclosure of such patent is incorporated herein by reference.

FIG. 3 illustrates the architecture of information processor 52 in accordance with a presently preferred embodiment of the invention. Camera 48 is connected through camera scan control electronics 60 to direct memory access (DMA) electronics 62, which essentially performs an interface function for obtaining camera data and loading such data into a common memory 64, for retrieving data from memory 64 and loading the data into a systolic array processor 66, and for returning processed data from systolic array processor 66 to memory 64. A high-speed 64-bit data bus 68 interconnects DMA 62 and memory 64 with a data-dependent processor 72 and a master computer 74. Camera scan control 60, DMA 62, memory 64, systolic array processor 66, data dependent processor 72 and master computer 74 are also interconnected by a lower-speed 32-bit- control bus 70. In general, master computer 74 controls and coordinates operation of the remainder of the information processor architecture, illustrated in FIG. 3, in the manner to be described in detail hereinafter in conjunction with the individual information processor components.

Figure 4:
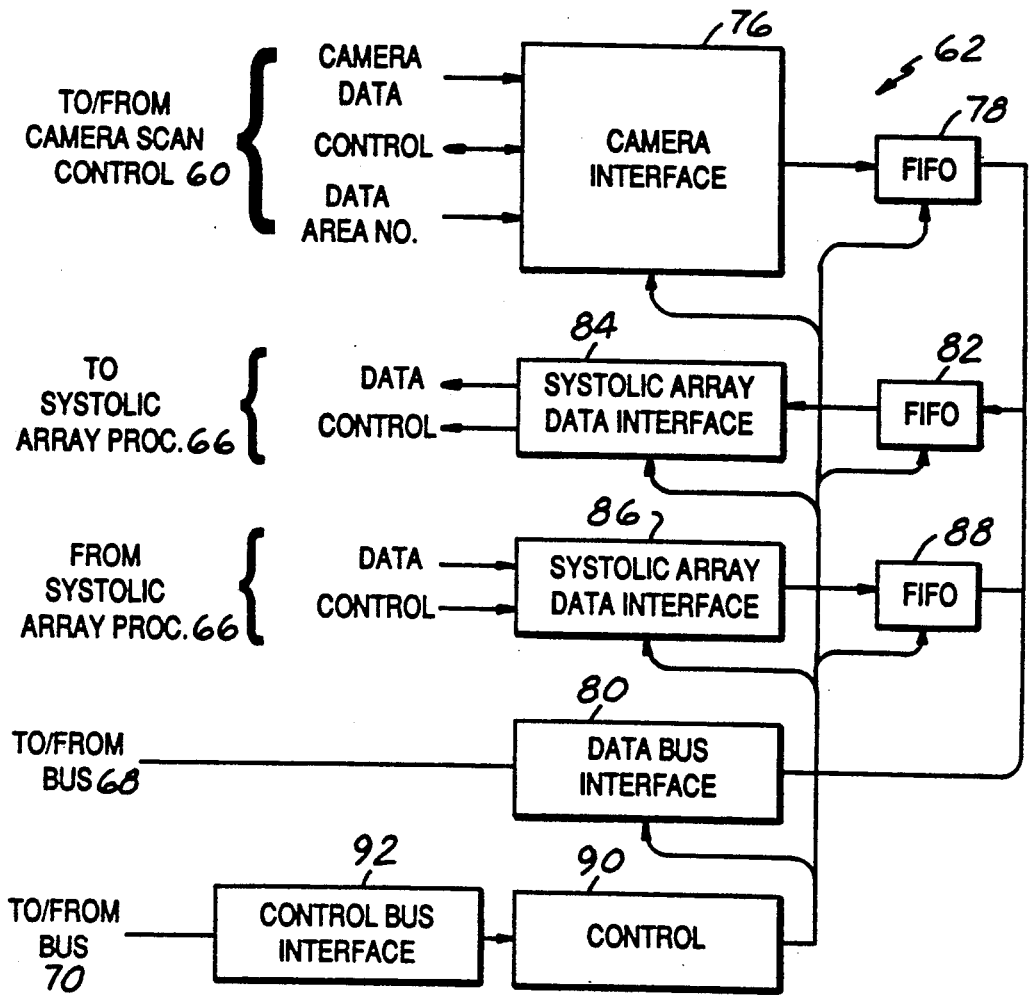
FIG. 4 is a functional block diagram of the direct memory access or DMA electronics illustrated in FIG. 2.

FIG. 4 is a functional block diagram of DMA electronics 72. A camera interface 76 receives image pixel data and information indicative of data area number from camera scan control 60 (FIG. 3), and both receives and transmits control signals from and to the camera scan controller. The internal data output of interface 76 is connected to data bus 68 (FIG. 3) through a FIFO register 78 and through data bus interface electronics 80. Data bus interface 80, which is bidirectional, is also connected through a FIFO register 82 and a systolic array data interface 84 to provide data and control signals to systolic array processor 66. A second systolic array data interface 86 receives data and control signals from the systolic array processor 66, and provides processed data through a FIFO register 88 to data bus interface 80. All of the electronics of DMA circuitry 62 are controlled by a microcoded control module 90, which receives instructions from master computer 74 (FIG. 3) through control bus 70 and control bus interface electronics 92.

In general, DMA electronics 62 has internal microcoded control 90 responsive to master controller 74 (FIG. 3) for controlling transfer of data between common memory 64, camera 48 and systolic array processor 66. For example, image pixel data from image data areas of interest may be down-loaded from the camera, and fed through FIFO register 78 and interface 80 to memory 64 via bus 68. At the same time, image data in memory 64 may be transmitted for processing to systolic array processor 66, or transmitted from processor 66 back to memory 64. FIFO registers 78,82,88 function as memory buffers, and permit such data transfer operations to be performed simultaneously while restricting access to data bus 68 and memory 64 to only a single function at any given time.

Figure 5:
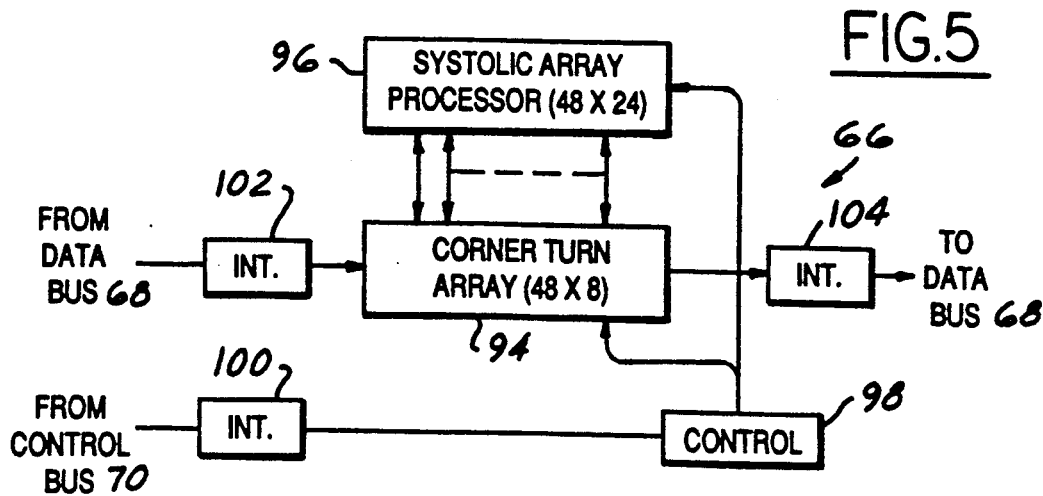
FIG. 5 is a functional block diagram of the systolic array processor illustrated in FIG. 2.

FIG. 5 is a functional block diagram of systolic array processor 66. Systolic array processor 66 comprises two systolic arrays 94,96. Each array 94,96 comprises a matrix of one-bit processors interconnected in a rectangular raster-type array arrangement. In the preferred embodiment of the invention herein disclosed, array 94 comprises a 48×8 array of one-bit processors for performing a "corner turn" operation on bit-parallel data from and to memory 64, and transferring such data bit-serial into and out of array 96 (as will be described in detail in connection with FIG. 10). Processor array 96 comprises a matrix of 48×24 one-bit processors. Each of the processor arrays 94,96 is controlled by associated microcoded control electronics 98, which in turn receives control instructions from control bus 70 and master controller 74 through interface electronics 100.

Input data from data bus 68 is received through interface 102, and output data is returned to memory 64 through interface electronics 104 and bus 68.

In the disclosed embodiment of the invention in which systolic array 96 comprises a 48×24 array of one-bit processors, there are thus 1152 one-bit processors in the array, which can simultaneously operate on 1152 image pixel data bytes, as distinguished from operating on a single byte at a time as in conventional VonNeuman processors. In a presently preferred implementation of the invention, systolic arrays 94,96 comprise arrays of one-bit geometric arithmetic parallel processor chips marketed by NCR under the designation NCR45CG72. General operation of these systolic array processor chips is described in a series of articles published by NCR in *Electronic Design* magazine on Oct. 31, Nov. 15, Nov. 29 and Dec. 13, 1984, and on Jan. 10, 1985. The specific NCR45CG72 systolic array processor chips employed in implementation of the present invention are also described in the associated manufacturer data sheet (pages 1–12). Both of these publications are incorporated herein by reference for purposes of background discussion on structure, function and operation of systolic array processors.

Figure 6:
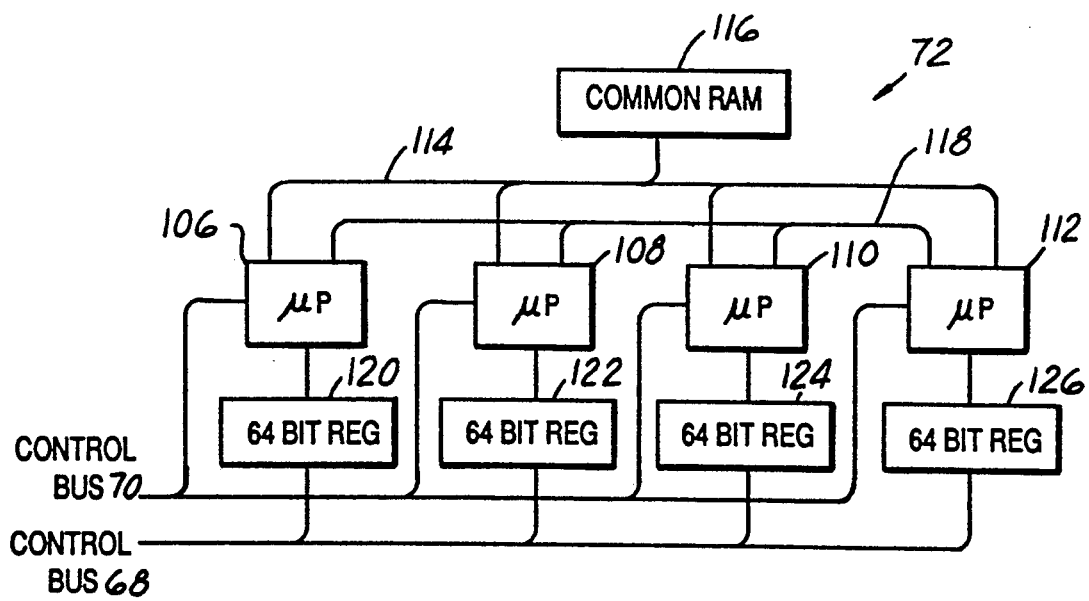
FIG. 6 is a functional block diagram of the data-dependent processor illustrated in FIG. 2.

FIG. 6 is a functional block diagram of data dependent processor 72 (FIG. 3). Data dependent processor 72 comprises a closely coupled array of four conventional VonNeuman microprocessors 106,108,110,112 having data and address buses 114 interconnected to each other and to a common random access memory 116. Processors 106,108,110,112, which comprise 68020 microprocessors in the presently preferred implementation of the invention, are also interconnected by an interrupt bus 118. Each microprocessor communicates with master computer 74 (FIG. 3) by means of control bus 70. Each microprocessor receives data from data bus 68 by means of an associated 64-bit register 120,122,124 and 126. Data bus 68 preferably comprises a 64-bit data bus as previously noted. In the presently preferred implementation of the invention, each image pixel byte comprises eight bits, 0,1, . . . 7. Thus, each register 120–126 is capable of storing eight bytes of image pixel data. (Preferably, each microprocessor 106,108,110 and 112 has a single bus port, and a bus controller not shown selectively connects each port to bus 70, 114 and 118 as appropriate. The functional illustration of FIG. 6 is for purposes of simplicity.)

Each time one of the microprocessors 106–112 requests pixel data from memory 64, the microprocessor commands down-loading not only of the particular byte of pixel data requested, but also the next seven bytes of pixel data stored in the next seven locations of memory 64. These eight consecutive bytes of pixel data are loaded into the associated 64-bit register 120–126. The requesting microprocessor then up-loads the desired byte of pixel data and performs appropriate processing. The next time the microprocessor is to request pixel data, the associated 64-bit register is first checked to see if the desired byte of pixel data is already stored therein. If so, the desired byte is up-loaded into the microprocessor without requiring access to the data bus and common memory. Since conventional data-dependent image processing algorithms performed in the microprocessors 106–112 typically involve a high percentage of operations on sequential or a substantially sequential image pixel bytes, the desired image pixel data is often found in the local register memory, thus not only greatly enhancing efficiency of the data-dependent processing, but also greatly reducing needed access to the common buses and memory, and thereby enhancing efficiency of other processing operations.

As disclosed in U.S. Pat. No. 4,958,223 incorporated by reference hereinabove, data areas at camera 48 are scanned at increments of container rotation, which preferably comprise increments of actual container rotation as indicated by position encoder 28 (FIG. 1), but which may comprise time increments during container rotation at constant velocity. FIG. 2 illustrates two such data areas 128 at the right edge of the container finish at threads 38, and 130 centrally of the container finish and essentially intersecting the container axis 23 (FIG. 1). The manner in which these (and other) data areas are selected and the processing is done at the camera itself are the subject of the referenced U.S. patent. In accordance with a further feature of the present invention illustrated in FIG. 7, image data is loaded by DMA electronics 62 into common memory 64, under control of master controller 74, in blocks by data area.

For example, on a first scan, the pixels of data area 128 are loaded into a first line 128-1 of memory block 64a. Where camera array 54 comprises a 512×256 element array (in the orientation illustrated in FIG. 2), the first line 128-1 of memory block 64a contains 256 image pixel bytes. The image pixel data from the second data area 130 is then loaded into memory block 64a, not in the next line after line 128-1, but into a later line 130-1. On the next increment of container rotation, the pixel data scanned from data area 128 is loaded into the line 128-2 immediately after data line 128-1 for the same data area at the first scan increment. Likewise, pixel data from area 130 is stored on the second scan in line 130-2 immediately after line 130-1. On the next scan, the third scan of data area 128 is loaded at line 128-3 immediately after the first and second scan lines, etc. In this way, following a complete revolution of the container, all of the pixel data from the camera data area 128 is loaded into a contiguous area within memory block 64a, all of the pixel data from camera data area 130 is located into an adjacent contiguous area of the memory block, etc. If there are 360 scan increments per container revolution, for example, there would be 360 consecutive scan lines for data area 128, as shown in FIG. 7, 360 consecutive scan lines for data area 130, etc.

Figure 8:
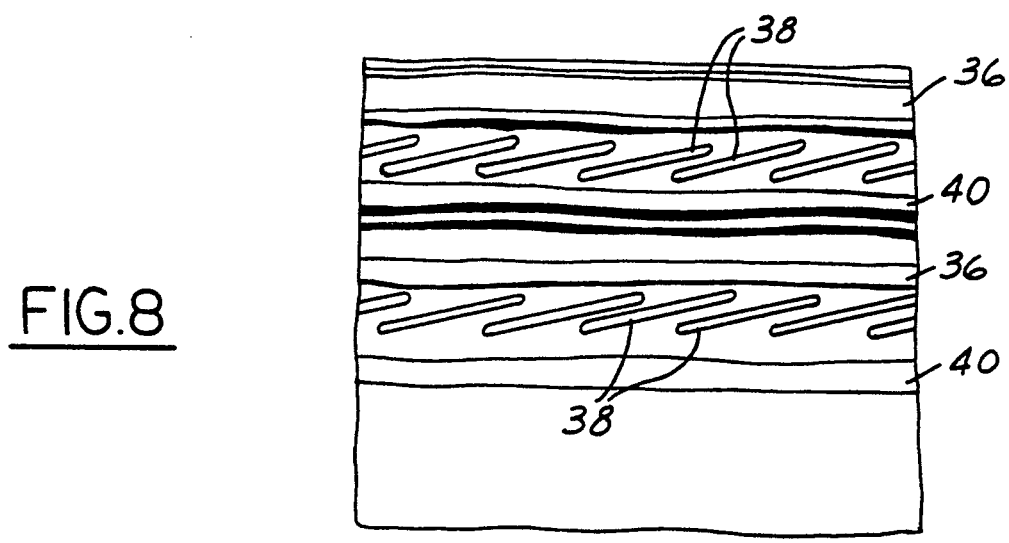
FIG. 8 is a schematic illustration of container finish data stored in FIG. 7.

The effect of this data storage technique is that each block of data effectively provides an "unwrapped" image of the particular area of the container finish viewed by that camera data area. For example, FIG. 8 illustrates the unwrapped image of data area 130. The slanted lines in the upper portion of FIG. 8 are the image of container threads 38 on the back side of the container finish as seen through the finish by the camera. The slanted lines in the lower portion of the figure are the image of threads 38 on the near side of the container finish. The lines between the images of the threads are the image of shoulder 40 on the back side of the container finish, and the image of sealing surface 36 on the near side of the container finish. Thus, from top to bottom in FIG. 8, camera 48 sees the far side of sealing surface 36, threads 38 on the back side of the container finish, shoulder 40 on the back side of the container finish, sealing surface 36 on the near side of the container finish, threads 38 on the near side of the container finish and shoulder 40 on the near side of the container finish. Block storage of image data as so described is particularly useful in performing analysis on image data from within a particular image data blocks, as will be described hereinafter.

Figure 9:
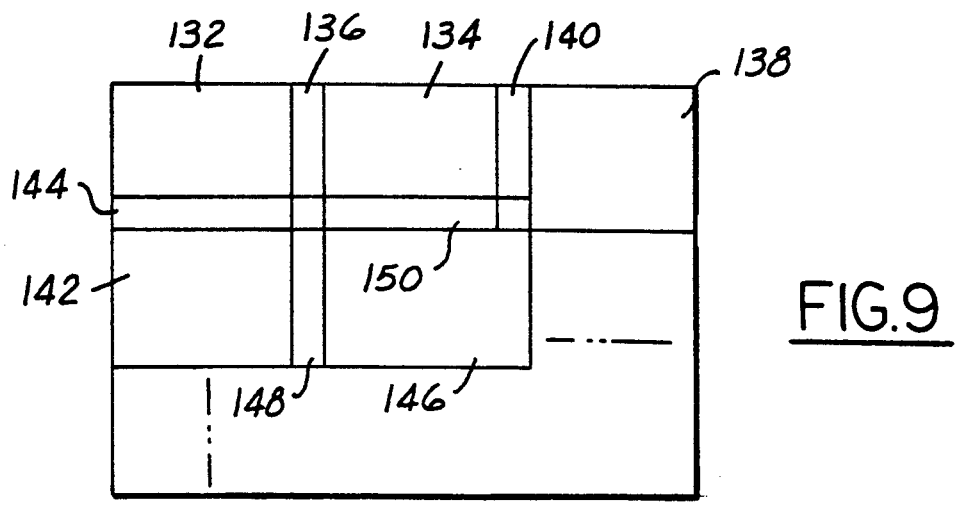
FIG. 9 is a schematic illustration of a technique for retrieving data from memory for processing in accordance with another feature of the present invention.

Systolic processor array 96 (FIG. 5) hereinabove described embodies 1,152 one-bit processors, each of which operates on one pixel byte (eight bits) at one time. In a camera 48 that employs a CCD array 54 (FIG. 2) of 512×256 CCD sensing elements, as shown in FIG. 2, there are thus over 130,000 pixels available for analysis. Furthermore, image data is obtained for at least one complete container revolution before analysis begins which, for 360 scan increments per revolution, implies a total of over 47 million image pixels available for processing. The above-referenced Pat. No. 4,958,223 discloses techniques for performing partial image processing on the camera array itself, and otherwise for reducing the amount of information for processing within the information processor. However, even with such information reduction, systolic processor array 96 cannot operate on all of the pixel data bytes simultaneously. FIG. 9 illustrates a further feature of the present invention whereby data is selectively removed from memory and subjected to processing in systolic array 96.

Figure 7:
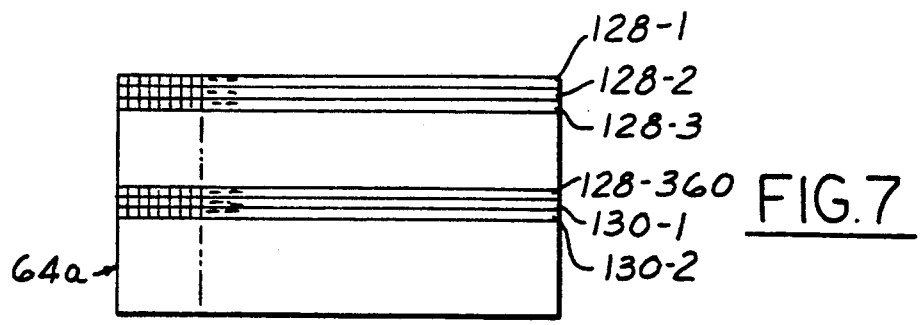
FIG. 7 is a schematic illustration of pixel data storage and retrieval in accordance with one feature of the present invention.

More specifically, memory block 64b in FIG. 9 represents a block of image data in memory (such as the entire block 128-1 through 128-360 in FIG. 7). DMA circuitry 62 (FIG. 3) first withdraws the sub-block 132 for processing in systolic array processor 66. Upon completion of such processing, the processed data is returned to memory, and block 134 is removed for processing. Block 134 overlaps block 132 in the area 136. Likewise, upon return of the processed data from block 134, block 138 is withdrawn for processing, overlapping block 134 in the area 140. Block 142 is next withdrawn, overlapping block 132 in the area 144. Block 146 is next withdrawn, overlapping block 142 in the area 148, and overlapping block 134 in the area 150. This process is repeated until the entire data block 64b has been processed. Overlap of data sub-blocks withdrawn for processing is particularly important in processing image data because of edge effects between adjacent data sub-blocks. For example, many image processing algorithms involve comparison of adjacent image pixel bytes within a given scan or from successive scans. Overlapping of image segments for processing as hereinabove described in conjunction with FIG. 9 eliminates the possibility that important information will be lost by reason of being at the edge of adjacent sub-blocks of image data.

As previously noted, systolic processor array 96 in the preferred implementation of the invention comprises a 48×24 array of one-bit processors. Each processor is adapted to process an eight-bit byte of image data, corresponding to one eight-bit pixel obtained from a data area of the camera. Each eight-bit pixel byte is loaded bit-parallel and in sequence—i.e., byte-serial—by DMA 62 into memory 64. However, when loading the data into systolic array 96, the data must be loaded byte-parallel for the entire block, and bit-serial within each byte. That is, the "zero" bits of all 1,152 pixel bytes are loaded simultaneously, the "one" bits are next loaded simultaneously, the "two" bits next loaded simultaneously, etc. A technique for accomplishing this with corner turn array 94, in accordance with another feature of the present invention, is illustrated in FIG. 10.

Figure 10:
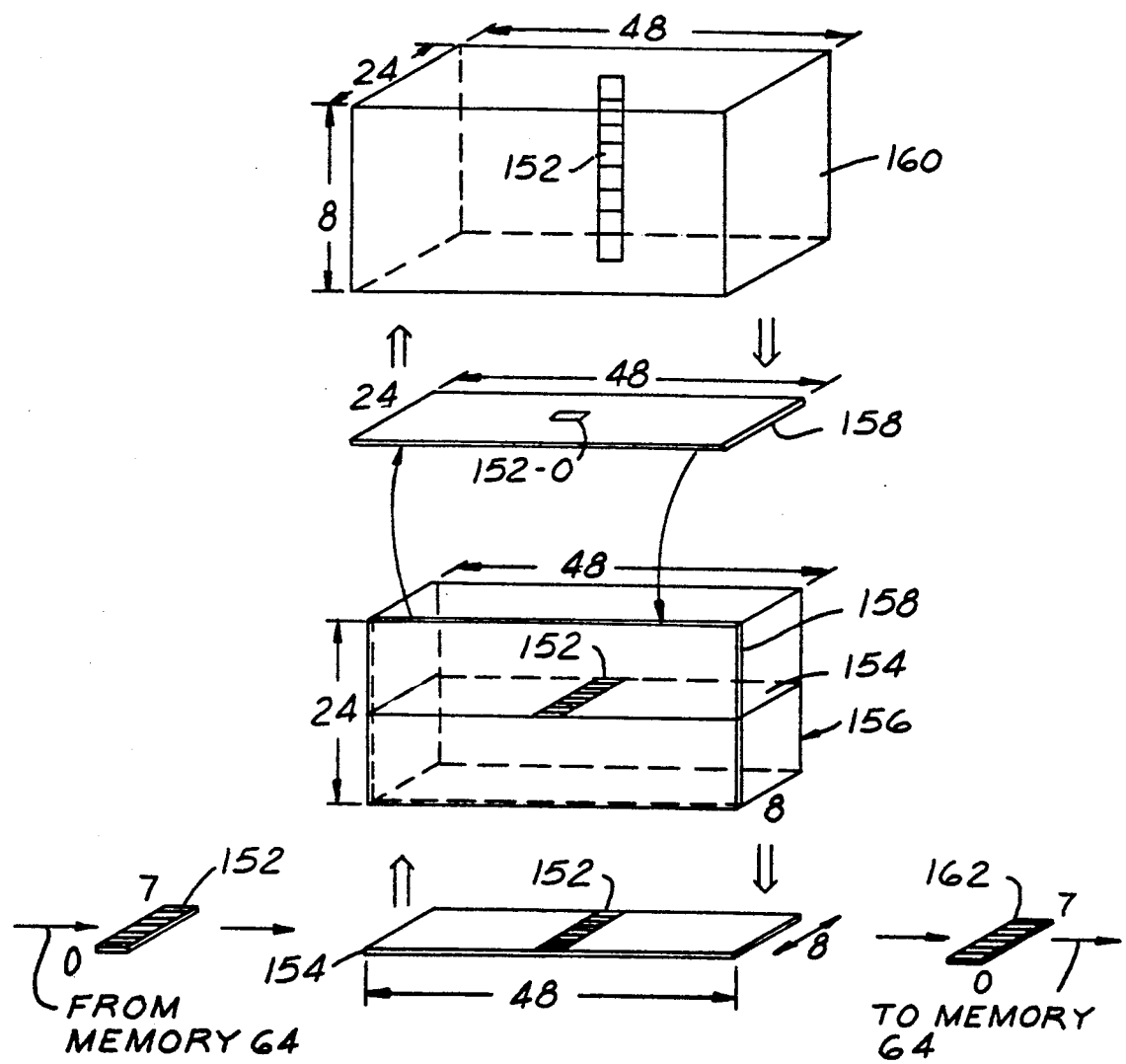
FIG. 10 is a schematic diagram that illustrates transmission of data to, from and within the systolic array processor illustrated in FIGS. 2 and 5.

At the lower left of FIG. 10, an eight-bit pixel byte is illustrated as being received by array 94 (FIG. 5) from common memory 64. Forty-eight of these bytes are sequentially loaded into corner turn array 94 to form what can be envisioned as a 48×8 data plane 154 that is one-bit high. Data plane 154 is then shifted within array 94 (upward as viewed in FIG. 10), and new data bytes are loaded into array 94 to form a new plane 154. This process is repeated twenty-three times, effectively to form within array 94 a rectangular data block 156 that is forty-eight bits long, eight bits deep and twenty-four bits high. Byte 152 and plane 154 are illustrated as being at about the middle of block 156. The "zero" bit of byte 152, and indeed the "zero" bits of all pixel bytes in block 156, are along the foremost edge of planes 154 and block 156.

As a next step, all of the "zero" bits in data block 156 are removed to form a second data plane 158 that is now forty-eight bits long, twenty-four bits deep and one bit high. This data plane is loaded simultaneously into the 1,152 one-bit processors of array 96. This process is repeated seven additional times, first with the plane of "one" bits in block 156, then with the plane of "two" bits, etc. Thus, the goal of loading all of the image bytes byte-parallel and bit-serial into systolic processor array 96 has been accomplished, forming in effect in array 96 a data block 160 that is forty-eight bits long, twenty-four bits wide and eight bits high. Desired data processing can now take place in array 96 under control of microcode 98 (FIG. 5).

When data is to be removed from array 96 following sequential parallel processing therein, the process of FIG. 10 is reversed. That is, the data is first withdrawn byte-parallel and bit-serial in planes 158 and loaded into corner turn array 94, starting with a plane 158 of "seven" bits, then a plane 158 of "six" bits, etc. Data 156 in array 94 is then shifted downwardly (FIG. 10) to form bit-parallel byte-serial planes 154, and the processed image pixel bytes 162 are withdrawn from planes 154 and returned bit-parallel byte-serial to memory 64.

The embodiment of the invention hereinabove disclosed thus includes the combination of systolic array processing, which can be microcoded efficiently to run any algorithm requiring a high degree of parallelism and not limited to a few fixed algorithms, and a tightly coupled array of data-dependent VonNeuman processors that can be microcoded for efficient data-dependent and/or non-sequential processing. Parallel and non-parallel processing can be divided between the respective processors, and can proceed in parallel. Other algorithms can be divided so that processing toggles between the two types of processors, with certain parameters being calculated by one type of processor and given as inputs to the other type of processor under control of master computer 74. It will be recognized, of course, that although the preferred embodiment of the invention has been disclosed in conjunction with eight-bit image pixel bytes, the principles of the present invention are in no way limited thereto.

I claim:

1. A machine vision system that includes:
    camera means for obtaining an image that comprises a plurality of pixels each forming a portion of the image,
    a memory for receiving and storing pixel data from said camera means,
    systolic array processing means that includes a plurality of one-bit data processing means configured in a rectangular array and means for controlling operation of said plurality of one-bit data processing means to process data simultaneously and in parallel,
    data-dependent and/or non-sequential processing means for performing data-dependent processing of image data, and
    control means including means for obtaining pixel data from said camera means and storing such data by pixel in said memory, means for retrieving pixel data from said memory and loading such data by pixel into said systolic array procesing means such that each of said plurality of one-bit processing means receives and operates on one byte of pixel data, means for returning data from said systolic array processing means to said memory, and means for retrieving pixel data from said memory and loading such data into said data-dependent processing means,
    said means for retrieving pixel data from memory and loading such data by pixel into said systolic array processing means including means for retrieving such data bit-parallel by pixel byte from said memory, said systolic array processing means comprising means for loading said data bit-serial by byte into individual one-bit processing means,
    said systolic-array processing means comprising first and second systolic array processors, means for serially storing a plurality of bit-parallel pixel bytes in said first processor, and means for obtaining all bits of a given significance from said first processor and loading siad bits simultaneously into said second processor.

2. The system set forth in claim 1 wherein said systolic array processing means, said data-dependent processing means and said control means respectively includes separate data processing means, and wherein said system further comprises at least one bus interconnecting said systolic array processing means, said data-dependent processing means and said control means for transmitting data and control information among said separate data processing means.

3. The system set forth in claim 2 further comprising means coupled to said bus for controlling access to said memory by said separate data processing means.

4. The system set forth in claim 3 wherein said memory access-controlling means comprises separate interface means coupled to said systolic array processing means for loading data into and retrieving data from said systolic array processing means.

5. The system set forth in claim 4 wherein said memory access-controlling means further comprises interface means coupled to said camera means for obtaining pixel data from said camera means, and means interconnecting all of said interface means to said memory.

6. The system set forth in claim 5 wherein all of said interface means include memory means for permitting said interface means to operate simultaneously.

7. The system set forth in claim 2 wherein said data-dependent processing means comprises at least one processor and a multi-byte register connecting said processor to said bus, means responsive to a data request from said processor to load multiple sequential data bytes from said memory into said multi-byte register, and means for searching for desired data in said register before requesting data from said memory.

8. The system set forth in claim 7 wherein said data-dependent processing means comprises a plurality of closely coupled VonNeuman processors.

9. The system set forth in claim 1 wherein said systolic array processing means further comprises means for obtaining all bits of a given significance from said second processor and loading said bits simultaneously into said first processor, and means for serially transmitting a plurality of bit-parallel bytes from said first processor to said memory.

10. The system set forth in claim 1 wherein said means for obtaining pixel data from said camera means and storing such data by pixel in memory comprises means for selectively obtaining pixel data from said camera means by data area on said camera means, and means for storing pixel data by data area in adjacent locations of said memory.

11. The system set forth in claim 1 wherein said means for retrieving pixel data from memory comprises means for sequentially retrieving pixel data from adjacent overlapping blocks of said memory.

12. The system set forth in claim 1 for inspecting transparent containers for variations affecting comemrcial acceptability of such contaienrs further comprising means for directing light energy into the container, said camera means being positioned to have a field of view that incldues portions of at least one wall surface of the container so as to obtain a said image of the container wall portion.

13. A machine vision system that comprises:
   camera means for obtaining an image in the form of a plurality of pixels each forming a portion of the image,
   means including a memory coupled to said camera means for receiving and storing pixel data from said camera means,
   systolic array processing means that includes a plurality of one-bit data processing means configured in a rectangular array of N×M processors, and means for controlling operation of said plurality of one-bit data processing means to process data simultaneously and in parallel, and
   means for transferring pixel data between said memory and said systolic array processing means in a bit-parallel configuration serially by byte at least oen byte at a time, each said byte of pixel data comprising n bits, $0, 1, \ldots n-1$,
   said systolic array processing means comprising means for loading said data bits serially by byte into individual one-bit processing means including a first systolic array of N×n processors, means for loading N×M bytes of bit-parallel pixel data serially by byte into said first systolic array, a second systolic array of N×M processors, and means for loading pixel data byte-parallel by bit from said first array into said second array.

14. The system set forth in claim 13 wherein said systolic array processing means further comprises means for transferring pixel data byte-parallel by bit from said seconda rray to said first array, and means for transferring pixel data bit-parallel by byte from said first array to said memory.

* * * * *